(12) United States Patent
Yamamoto

(10) Patent No.: US 6,392,073 B1
(45) Date of Patent: May 21, 2002

(54) INTERMEDIATES AND PROCESSES FOR THE PREPARATION OF OPTICALLY ACTIVE OCTANOIC ACID DERIVATIVES

(75) Inventor: Hisashi Yamamoto, Aichi (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/947,439

(22) Filed: Sep. 7, 2001

Related U.S. Application Data

(62) Division of application No. 09/700,181, filed as application No. PCT/JP99/02427 on May 11, 1999.

(30) Foreign Application Priority Data

May 12, 1998 (JP) .......................................... 10-128901

(51) Int. Cl.⁷ .............................................. C07C 51/00
(52) U.S. Cl. ..................................................... 554/154
(58) Field of Search ......................................... 554/154

(56) References Cited

FOREIGN PATENT DOCUMENTS

| JP | 7-316092 | 12/1995 | ............ C07C/53/21 |
|---|---|---|---|
| JP | 8-291106 | 11/1996 | ............ C07C/57/18 |
| JP | 8-295648 | 11/1996 | ......... C07C/53/126 |

OTHER PUBLICATIONS

Hasegawa et al., Synlett, No. 8, pp. 882–884, Aug., 1998.*
Oppolzer, Wolfgang, et al., "Enantioselective synthesis of the Prelog–Djerassi Acid via Group–Selective Aldolization/Desymmetrization of a Meso Dialdehyde with a Chiral N–Propionylsultam" Tetrahedron Letters, vol. 38, No. 5 pp. 809–812, 1997.
Ayoub, Mimoun, et al., "Diastereoselective Alkylation of Sultam–Derived Amino Acid Aldimines Preparation of Cα–Methylated Amino Acids", Tetrahedron Letters, vol. 36, No. 23 pp. 4069–4072, 1995.

* cited by examiner

Primary Examiner—Laura L. Stockton
(74) Attorney, Agent, or Firm—Sughrue Mion, PLLC

(57) ABSTRACT

Novel intermediates, i.e., N-(2S-(2-propenyl)octanoyl)-(1S)-(−)-2, 10-camphorsultam, N-(2S-(2-propynyl)octanoyl)-(1S)-(−)-2,10-camphorsultam and N-(2R-(2-propyl)octanoyl)-(1S)-(−)-2,10-camphorsultam; processes for the preparation of the intermediates; and processes for the preparation of optically active 2S-(2-propenyl)octanoic acid, 2S-(2-propynyl)octanoic acid and 2R-propyloctanoic acid by using the same. Optically active 2R-propyloctanoic acid equivalent or superior to that prepared by the process of the prior art in optical purity can be efficiently prepared in shorter reaction steps.

5 Claims, No Drawings

US 6,392,073 B1

INTERMEDIATES AND PROCESSES FOR THE PREPARATION OF OPTICALLY ACTIVE OCTANOIC ACID DERIVATIVES

CROSS REFERENCE TO RELATED APPLICATION

This is a divisional of application Ser. No. 09/700,181, filed Nov. 13, 2000, which is a 371 of PCT/JP99/02427, filed May 11, 1999, the disclosures of which are incorporated herein by reference. PCT/JP99/02427 was published in Nov. 18, 1999 under PCT Article 21(2) in Japanese.

TECHNICAL FIELD

The present invention relates to novel intermediates, processes for the preparation thereof and processes for the preparation of optically active octanoic acid derivatives by using intermediates.

More particularly, the present invention relates to novel intermediates, i.e., N-(2S-(2-propenyl)octanoyl)-(1S)-(−)-2,10-camphorsultam, N-(2S-(2-propynyl) octanoyl)-(1S)-(−)-2,10-camphorsultam and N-(2R-(2-propyl) octanoyl)-(1S)-(−)-2,10-camphorsultam; processes for the preparation thereof; and processes for the preparation of optically active 2S-(2-propenyl)octanoic acid, 2S-(2-propynyl)octanoic acid and 2R-propyloctanoic acid by using thereof intermediates.

BACKGROUND ART

The optically active octanoic acid derivatives prepared by the present invention are intermediates useful for the preparation of medicaments or are compounds useful as medicaments. For example, a racemate of 2R-propyloctanoic acid is described in Example 7(33) of JP-A-7-316092 as an agent for treating or preventing neurodegenerative diseases derived from functional abnormality of astrocytes.

As a result of the study after that, it was found that optically active 2R-propyloctanoic acid has strong activities in particular. Accordingly, methods for obtaining this compound efficiently have been studied variously, and the following processes are known until now.

For example, JP-A-8-291106 discloses a method by optical resolution using optically active amine. However, in the process of optically separating 2R-propyloctanoic acid from its racemate, both the chemical yield (total synthetic yield of 5.9% at 6 stages from dimethyl hexylmalonate) and the optically purity (90.0% e.e.) were so insufficient that the process had no practical use.

A process using an optically active starting material is known as other process for obtaining optically active 2R-propyloctanoic acid. For example, JP-A-8-295648 discloses a process using optically active prolinol. An optically active branched alkanoic acid having a high optical purity (96.0% e.e.) can be prepared using this process. However, the chemical yield (total synthetic yield of 20.1% at 5 stages from pentanoyl chloride) was so insufficient that the process did not necessarily have a practical use.

DISCLOSURE OF THE INVENTION

The present inventor has found that novel intermediates, i.e., N-(2S-(2-propenyl) octanoyl)-(1S)-(−)-2,10-camphorsultam, N-(2S-(2-propynyl) octanoyl)-(1S)-(−)-2,10-camphorsultam and N-(2R-(2-propyl)octanoyl)-(1S)-(−)-2,10-camphorsultam, by using optically active (1S)-(−)-2,10-camphorsultam, further processes for the preparation of optically active 2S-(2-propenyl)octanoic acid, 2S-(2-propynyl)octanoic acid and 2R-propyloctanoic acid as high optical purity (95–99% e.e.) by using thereof intermediates, accomplished the present invention.

That is, the present invention relates to novel intermediates, processes for the preparation thereof and processes for the preparation of optically active octanoic acid derivatives by using intermediates as follows:

[1] A compound of N-(2S-(2-propenyl)octanoyl)-(1S)-(−)-2,10-camphorsultam, N-(2S-(2-propynyl) octanoyl)-(1S)-(−)-2,10-camphorsultam, or N-(2R-(2-propyl)octanoyl)-(1S)-(−)-2,10-camphorsultam;

[2] A compound of N-(2S-(2-propenyl)octanoyl)-(1S)-(−)-2,10-camphorsultam depicted in [1];

[3] A compound of N-(2S-(2-propynyl)octanoyl)-(1S)-(−)-2,10-camphorsultam depicted in [1];

[4] A compound of N-(2R-(2-propyl)octanoyl)-(1S)-(−)-2,10-camphorsultam depicted in [1];

[5] A process for the preparation of N-(2S-(2-propenyl) octanoyl)-(1S)-(−)-2,10-camphorsultam depicted in [2], which is characterized by the reaction of N-octanoyl-(1S)-(−)-2,10-camphorsultam with allyl halide;

[6] A process for the preparation of N-(2S-(2-propynyl) octanoyl)-(1S)-(−)-2,10-camphorsultam depicted in [3], which is characterized by the reaction of N-octanoyl-(1S)-(−)-2,10-camphorsultam with propargyl halide;

[7] A process for the preparation of N-(2R-(2-propyl) octanoyl)-(1S)-(−)-2,10-camphorsultam depicted in [4], which is characterized by the reduction of N-(2S-(2-propenyl)octanoyl)-(1S)-(−)-2,10-camphorsultam depicted in [2];

[8] A process for the preparation of N-(2R-(2-propyl) octanoyl)-(1S)-(−)-2,10-camphorsultam depicted in [4], which is characterized by the reduction of N-(2S-(2-propynyl)octanoyl)-(1S)-(−)-2,10-camphorsultam depicted in [3];

[9] A process for the preparation of optically active 2S-(2-propenyl)octanoic acid, which is characterized by the hydrolysis of N-(2S-(2-propenyl) octanoyl)-(1S)-(−)-2,10-camphorsultam depicted in [2];

[10] A process for the preparation of optically active 2R-propyloctanoic acid, which is characterized by the reduction of optically active 2S-(2-propenyl) octanoic acid obtained in [9];

[11] A process for the preparation of optically active 2S-(2-propynyl)octanoic acid, which is characterized by the hydrolysis of optically active N-(2S-(2-propynyl) octanoyl)-(1S)-(−)-2,10-camphorsultam depicted in [3]

[12] A process for the preparation of optically active 2R-propyloctanoic acid, which is characterized by the reduction of optically active 2S-(2-propynyl) octanoic acid obtained in [11].

[13] A process for the preparation of optically active 2R-propyloctanoic acid, which is characterized by the hydrolysis of optically active N-(2R-(2-propyl) octanoyl)-(1S)-(−)-2,10-camphorsultam depicted in [4].

DETAILED EXPLANATION OF THE INVENTION

Optically active 2R-propyloctanoic acid in high optical purity (95–99% e.e.) and superior chemical yield (4 steps from octanoyl chloride, total synthetic yield 42.5–72.1%)

can be efficiently prepared by the method of the present invention. Further the hydrolysis of camphorsultam derivatives by using tetraalkylammonium hydroxide is novel reaction. This observation has been confirmed from experiments by the present inventor for the first time.

Novel intermediate compounds of the present invention can easily improve optical purity by recrystallization since novel intermediates compounds are easily crystallized. For example, the residue of the reaction was purified by column chromatography to give N-(2S-(2-propynyl)octanoyl)-(1S)-(−)-2,10-camphorsultam having 96.8% diastereoisomer excess (liquid chromatography). Further thus obtained compound could be improved to give it having 99.4% diastereoisomer excess (liquid chromatography) by recrystallization.

In the present invention, the process for the preparation of 2R-propyloctanoic acid may be carried out four methods (A) to (D) as follows, respectively.

(A) 2R-propyloctanoic acid may be prepared by reacting of camphorsultam with octanoic acid or its derivatives→the reaction of allyl halide→hydrolysis→reduction;
1) reacting of (1S)-(−)-2,10-camphorsultam with octanoic acid or its derivatives,
2) reacting of N-octanoyl-(1S)-(−)-2,10-camphorsultam with ally halide,
3) hydrolysis of N-(2S-(2-propenyl)octanoyl)-(1S)-(−)-2,10-camphorsultam, and
4) reduction of optically active 2S-(2-propenyl)octanoic acid.

(B) 2R-propyloctanoic acid may be prepared by reacting of camphorsultam with octanoic acid or its derivatives→the reaction of propargyl halide→hydrolysis→reduction;
1) reacting of (1S)-(−)-2,10-camphorsultam with octanoic acid or its derivatives,
2) reacting of N-octanoyl-(1S)-(−)-2,10-camphorsultam with propargyl halide,
3) hydrolysis of N-(2S-(2-propynyl)octanoyl)-(1S)-(−)-2,10-camphorsultam, and
4) reduction of optically active 2S-(2-propynyl)octanoic acid.

(C) 2R-propyloctanoic acid may be prepared by reacting of camphorsultam with octanoic acid or its derivatives→the reaction of allyl halide→reduction→hydrolysis;
1) reacting of (1S)-(−)-2,10-camphorsultam with octanoic acid or its derivatives,
2) reacting of N-octanoyl-(1S)-(−)-2,10-camphorsultam with ally halide,
3) reduction of N-(2S-(2-propenyl)octanoyl)-(1S)-(−)-2,10-camphorsultam, and
4) hydrolysis of N-(2S-(2-propyl)octanoyl)-(1S)-(−)-2,10-camphorsultam.

(D) 2R-propyloctanoic acid may be prepared by reacting of camphorsultam with octanoic acid or its derivatives→the reaction of propargyl halide→reduction→hydrolysis;
1) reacting of (1S)-(−)-2,10-camphorsultam with octanoic acid or its derivatives,
2) reacting of N-octanoyl-(1S)-(−)-2,10-camphorsultam with propargyl halide,
3) reduction of N-(2S-(2-propynyl)octanoyl)-(1S)-(−)-2,10-camphorsultam, and
4) hydrolysis of N-(2S-(2-propyl)octanoyl)-(1S)-(−)-2,10-camphorsultam.

The summary of the above four methods was shown in Scheme 1.

In the Scheme 1;

X represent elimination group generally known (e.g., p-toluenesulfonyl, methanesulfonyl, chloride, bromide or iodide atom etc.).

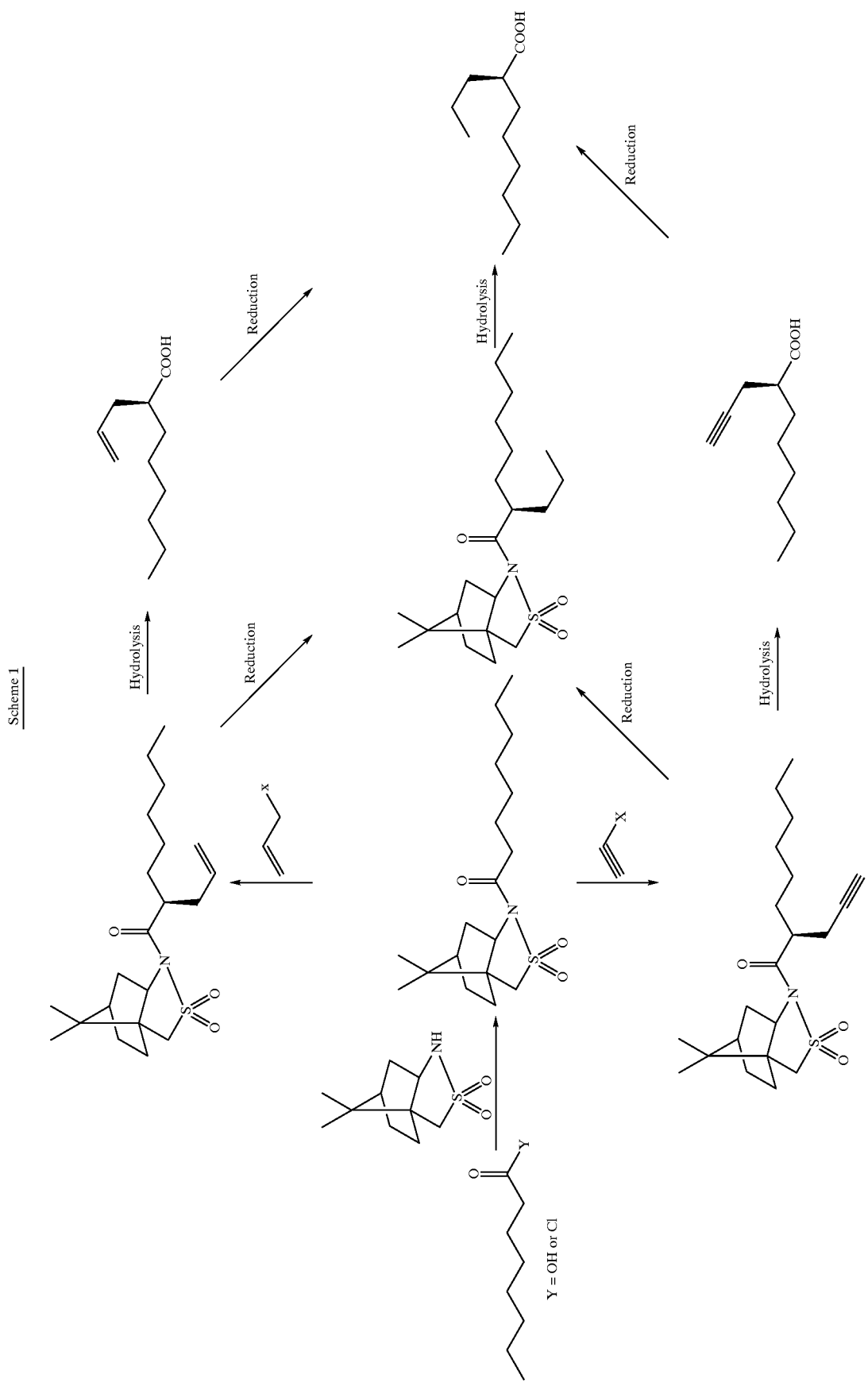

The reaction of (1S)-(-)-2,10-camphorsultam with octanoic acid or its derivatives is known per se (Tetrahedron, 48, 2453 (1992)), and may be carried out by, for example, using an acid halide.

The method using an acid halide may be carried out, for example, by reacting a octanoic acid with an acid halide (e.g., oxalyl chloride, thionyl chloride etc.) in an inert organic solvent (e.g., chloroform, dichloromethane, diethyl ether, tetrahydrofuran etc.) or without a solvent at from −20° C. to the reflux temperature of the solvent, and then by reacting octanoyl chloride obtained with (1S)-(-)-2,10-camphorsultam in the presence of an base [tertiary amine (e.g., pyridine, triethylamine, dimethylaniline, dimethylaminopyridine etc.), hydroxide of an alkali metal (e.g., sodium hydroxide, potassium hydroxide, etc.) or organic lithium (e.g., n-butyllithium, phenyllithium etc.)] in an inert organic solvent (e.g., chloroform, dichloromethane, diethyl ether, tetrahydrofuran, dimethylformamide, dimethylsulfoxide, toluene etc.), at a temperature of from 0° C. to 40° C., This reaction preferably may be carried out in an atmosphere of inert gas (e.g., argon, nitrogen etc.) under anhydrous conditions.

The alkylation of N-octanoyl-(1S)-(-)-2,10-camphorsultam with alkyl halide or propagyl halide may be carried out by using organic metal. The alkylation by using organic metal is known per se, and may be carried out, for example, by reacting N-octanoyl-(1S)-(-)-2,10-camphorsultam with allyl halide or propargyl halide in the presence or absence of an iodide of an alkali metal (e.g., lithium iodide, sodium iodide, potassium iodide, etc.) and in the presence of an base (e.g., n-butyllithium, sec-butyllithium, t-butyllithium, phenyllithium, diisoporopyllithium, potassium hydroxide, sodium hydroxide, etc.) in an inert organic solvent (e.g., tetrahydrofuran, dioxane, diethyl ether, benzene, dimethoxyehtane, hexane, cyclohexane, hexamehtlphosphoramide, dimethylindazolidione or a mixture of them, etc.), at a temperature of from −70° C. to 20° C.

The reduction of optically active 2S-(2-propenyl)octanoic acid, optically active 2S-(propynyl)octanoic acid, N-(2S-(2-propenyl)octanoyl)-(1S)-(-)-2,10-camphorsultam or N-(2S-(2-propynyl)octanoyl)-(1S)-(-)-2,10-camphorsultam may be carried out by using catalytic reduction.

The catalytic reduction is known per se, and may be carried out, for example, in an inert solvent (e.g., ethyl acetate tetrahydrofuran, tetrahydropyran, dioxane, diethoxyethane, diethyl ether, biphenyl ether, methanol, ethanol isopropanol, benzene, toluene, xylene, acetone, methyl ethyl ketone, phenyl methyl ketone, acetonitrile, hexamethylphosphoramide, dimethylformamide dimethylimizazolidine, mixture of them etc.), by using a catalyst (e.g., palladium on carbon, palladium, platinum, platinum oxide, nickel, palladium hydroxide on carbon, rhodium, rhodium on carbon, ruthenium, ruthenium on carbon, tris(triphenylphosphine)chlororhodium, etc.) under an atmosphere of hydrogen, at a temperature of from 0° C. to 60° C.

The hydrolysis of N-(2S-(2-propenyl)octanoyl)-(1S)-(-)-2,10-camphorsultam, N-(2S-(2-propynyl)octanoyl)-(1S)-(-)-2,10-camphorsultam or N-(2S-(2-propyl)octanoyl)-(1S)-(-)-2,10-camphorsultam may be carried out by methods as follows.
(i) The hydrolysis by using hydroxide of an alkali metal is known per se (Tetrahedron, 43, 1969 (1987) or Helv. Chim. Acta., 72, 1337 (1989)), and may be carried out, for example, in the presence or absence of a peroxide (e.g., hydroperoxide, t-butylhydroperoxide an aqueous solution them, etc.), by using hydroxide of an alkali metal (e.g., lithium hydroxide, sodium hydroxide, potassium hydroxide, an aqueous solution them, etc.) in a water-miscible solvent (tetrahydrofuran, dioxane, a mixture of water and them, etc.) at a temperature of from 0° C. to 40° C.

It is known that this reaction was proceeded without racemization and the obtained compound was given to maintain optical purity.
(ii) The hydrolysis by using tetraalkylammonium hydroxide is quite novel reaction.

This reaction may be carried out, for example, in the presence or absence of a peroxide (e.g., hydroperoxide, t-butylhydroperoxide an aqueous solution them, etc.) by using tetraalkylammonium hydroxide (e.g., tetrabutylammonium hydroxide, tetraoctylammonium hydroxide, tetradecylammonium hydroxide, an aqueous solution them, etc.) in a water-miscible solvent (tetrahydrofuran, dimethoxyethane, t-butanol, dioxane, a mixture of water and them, etc.) at a temperature of from −20° C. to 40° C. With the proviso that, when camphorsultam derivatives have double or triple bond, this reaction may be carried out in the presence of an excess amount of the compound having double bond (e.g., 2-methyl-2-butene, etc.) since the protection of the compound having double or triple bond is oxidized by peroxide.

It is known that this reaction was proceeded without racemization and the obtained compound was given to maintain optical purity.

Furthermore, optically active 2R-(2-propenyl)octanoic acid, 2R-(2-propynyl) octanoic acid or 2S-propyloctanoic acid may be prepared by the same procedure as the method of the present invention using (1R)-(+)-2,10-camphorsultam instead of (1S)-(-)-2,10-camphorsultam.

N-(2S-(2-propenyl)octanoyl)-(1S)-(-)-2,10-camphorsultam, N-(2S-(2-propynyl) octanoyl)-(1S)-(-)-2,10-camphorsultam and N-(2R-(2-propyl) octanoyl)-(1S)-(-)-2,10-camphorsultam in the present invention are not described in the literature, therefore they are novel compound. They are useful as intermediate of process for the preparation of 2R-propyloctanoic acid.

The racemate of 2S-(2-propenyl)octanoic acid as intermediate of the present invention is known per se, in the literature of Chem. Pharm. Bull., 24, 538 (1976). The racemate of 2S-(2-propynyl)octanoic acid is known per se, in the literature of Tetrahedron Lett., 25, 5323 (1984). (1S)-(-)-2,10-camphorsultam is known per se, as the CAS registry No. 94594-90-8. N-octanoyl-(1S)-(-)-2,10-camphorsultam is known per se, in the literature of Tetrahedron, 48, 2453 (1992). 2S-(2-propynyl)octanoic acid is known per se, in JP-A-8-291106.

EXAMPLES

The present invention is explained in detail based on the following examples, but the present invention is not limited thereto.

Example 1

Preparation of N-Octanoyl-(1S)-(-)-2,10-camphorsultam

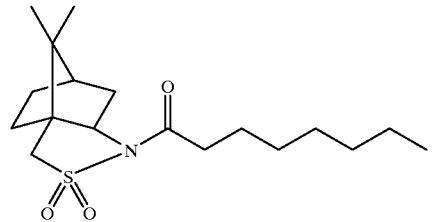

To a solution of (1S)-(-)-2,10-camphorsultam (15.0 g) in tetrahydrofuran (100 ml) was added triethylamine (14.6 ml) and dimethylaminopyridine (0.85 g). To this solution was added dropwise a solution of octanoyl chloride (12.5 g) in tetrahydrofuran (20 ml) at 0° C. The reaction mixture was stirred for 1 hour at 0° C. To the mixture was added water (14 ml), and concentrated. The residue was diluted with ethyl acetate, washed with 2N aqueous solution of hydrochloric acid, water, a saturated aqueous solution of sodium chloride (×2), 1N aqueous solution of sodium hydroxide (×2), water and a saturated aqueous solution of sodium chloride, successively, dried over anhydrous magnesium sulfate, and concentrated to give the title compound (24.0 g, 100% crude yield) having the following physical data.

TLC: Rf 0.33 (ethyl acetate: hexane=3:17); NMR (CDCl$_3$): δ 3.86 (1H, t, J=6.3 Hz), 3.49 (1H, d, J=13.2 Hz), 3.43 (1H, d, J=13.2 Hz), 2.72 (2H, dt, J=7.9, 2.6 Hz), 2.09 (2H, m), 1.88 (3H, m), 1.67 (2H, m), 1.31 (10H, m), 1.14 (3H, s), 0.96 (3H, s), 0.86 (3H, t, J=6.8 Hz);

IR (liquid film): ν 2957, 2930, 2857, 1698, 1458, 1414, 1375, 1331, 1271, 1237,1217, 1165, 1134, 1109,1065, 1040cm$^{-1}$.

Example 2

Preparation of N-(2S-(2-Propenyl)octanoyl)-(1S)-(−)-2,10-camphorsultam

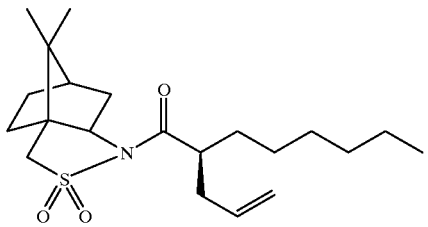

To a solution of diisopropylamine (20.0 ml) in tetrahydrofuran (40 ml) was added dropwise 1.6 M n-butyllithium in hexane solution (94 ml) at 0° C. The mixture was stirred for 30 minute at the same temperature. This solution was slowly added dropwise to the solution of the compound prepared in reference example 1 (52.2 9) in tetrahydrofuran (80 ml) at −72° C. After the mixture was stirred for 30 minute at the same temperature, and to this solution was added dropwise the mixture solution of allyl bromide (18 ml), a solution of lithiumiodide (3.7 g) in tetrahydrofuran (15 ml) and dimethylindazolidione (23 ml). The reaction mixture was stirred for 1 hour at −78° C., 4 hours at −20° C. and 1 hour at 0° C. The mixture was quenched by water, and concentrated. The residue was extracted with a mixture solution of hexane:ethyl acetate=1:1. The extract was washed with 2N aqueous solution of hydrochloric acid, water (×2), a saturated aqueous solution of sodium hydrogencarbonate and a saturated aqueous solution of sodium chloride, successively, dried over anhydrous magnesium sulfate, and concentrated. The residue was recrystallized from methanol (×2) to give the title compound (37.4 g, 71.7% yield (2 steps from (1S)-(−)-2,10-camphorsultam)) having the following physical data.

TLC: Rf 0.45 (hexane:ethyl acetate=17:3); NMR (CDCl$_3$): δ 5.80 (1H, ddt, J=15.6, 9.8, 7.2 Hz), 5.05 (1H, ddt, J=15.6, 2.2 Hz), 4.98 (1H, dd, J=9.8, 2.2 Hz), 3.90 (2H, t, J=6.3 Hz), 3.51 (1H, d, J=13.9 Hz), 3.42 (1H, d, J=13.9 Hz), 3.12 (1H, m), 2.36 (2H, t, J=7.0 Hz), 2.03 (2H, d, J=6.4 Hz), 1.88 (2H, m), 1.74 (1H, m), 1.26 (10H, m), 1.16 (3H, s), 0.96 (3H, s), 0.86 (3H, t, J=6.4 Hz); IR (KBr): ν 3075, 2994, 2857, 1682, 1640, 1471, 1445, 1418, 1401, 1327, 1291, 1273, 1252, 1238, 1217, 1167, 1136, 1117, 1069, 1042, 992, 947, 909 cm$^{-1}$; m.p.: 94–95° C.; diastereoisomer excess: 99% (liquid chromatography).

Example 3

Preparation of 2S-(2-Propenyl)octanoic Acid

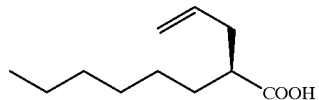

To a solution of the compound prepared in example 2 (10.0 g) in dimethoxyethane (10 ml) was added 2-methyl-2-butene (8.3 ml) and 30% aqueous solution hydrogen peroxide (5.4 ml) at −10° C. To vigorously stirring this mixture was added dropwise 40% aqueous solution tetrabutylammonium hydroxide (34 ml). The reaction mixture was stirred for 2 hours. The mixture was quenched by 2N aqueous solution of sodium sulfite (35 ml), and stirred for 1 hour at room temperature. To the mixture was added 1N aqueous solution of oxalic acid, and the mixture was extracted with a mixture solution of ethyl acetate:isopropyl ether=1:4. The extract was washed with 1N aqueous solution of oxalic acid, water (×2) and a saturated aqueous solution of sodium chloride, successively, dried over anhydrous sodium sulfate, and concentrated. To the residue was added a mixture solution of isopropyl ether and hexane=1:2, and insoluble matters were filtered. The filtrate was concentrated to give the title compound (5.72 g) having the following physical data.

TLC: Rf 0.46 (hexane:ethyl acetate=7:3);
NMR (CDCl$_3$): δ 5.78 (1H, ddt, J=17.0, 10.1, 6.9 Hz), 5.10 (1H, dd, J=17.0, 1.9 Hz), 5.05 (1H, dd, J=10.1, 1.9 Hz), 2.44 (2H, m), 2.30 (1H, m), 1.64 (1H, m), 1.55 (1H, m), 1.30 (8H, brs), 0.90 (3H, t, J=6.8 Hz); IR (neat): ν 2930, 2859, 1709, 1644, 1460, 1420, 1289, 1250, 1210, 992, 916 cm$^{-1}$; Optical purity: 99% e.e. (gas chromatography).

Example 4

Preparation of 2R-Propyloctanoic Acid

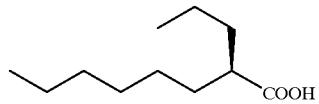

To the mixture solution of the compound prepared in example 3(a) (168 mg) in methanol (1.2 ml) and ethyl acetate (1.2 ml) was added 10% palladium carbon (17 mg). The mixture was stirred for 1 hour at room temperature under an atmosphere of hydrogen gas. The reaction mixture was filtrated through Celite (being on sale), and the filtrate was concentrated. The residue was purified by silica gel column chromatography (hexane:ethyl acetate=9:1→4:1) to give the title compound (109 mg, 74% yield (2 steps from the compound prepared in example 2)) having the following physical data.

TLC: Rf 0.46 (hexane:ethyl acetate=7:3); NMR (CDCl$_3$): δ 2.38 (1H, m), 1.55 (2H, m), 1.53–1.20 (12H, m), 0.94 (3H, t, J=6.8 Hz), 0.90 (3H, t, J=6.8 Hz); IR (neat): ν 2959, 2932, 1707, 1470, 1420, 1379, 1289, 1215, 943 cm$^{-1}$; Optical purity: 95.2% e.e. (liquid chromatography).

Example 5

Preparation of N-(2R-(2-Propyl)octanoyl)-(1S)-(−)-2,10-camphorsultam

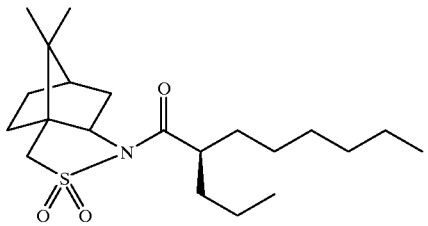

To 10% palladium carbon (500 mg, containing 60.7% in water) was added the mixture solution of the compound prepared in example 2 (2.0 g) in ethylacetate (7 ml) and dimethoxyethane (7 ml). The mixture was stirred for 1 hour at room temperature under an atmosphere of hydrogen gas. The reaction mixture was filtrated through Celite (being on sale), and the filtrate was concentrated. The residue was purified by silica gel column chromatography (hexane:ethyl acetate=9:1) to give the title compound (2.01 g, 100% yield) as a solid having the following physical data.

TLC: Rf 0.37 (hexane:ethyl acetate=9:1); NMR (CDCl$_3$): δ 3.90 (1H, t, J=6.3 Hz), 3.51 (1H, d, J=13.2 Hz), 3.43 (1H, d, J=13.2 Hz), 3.01, (1H, m), 2.07 (2H, m), 1.88 (3H, m), 1.77–1.19 (16H, m), 1.16 (3H, s), 0.97 (3H, s), 0.89 (3H, t, J=6.8 Hz), 0.83 (3H, t, J=6.8 Hz); IR (KBr): ν 2959, 2861, 1684, 1468, 1458, 1416, 1401, 1375, 1327, 1281, 1278, 1250, 1237, 1165, 1136, 1113, 1062, 1040 cm$^{-1}$; diastereoisomer excess: 99% (liquid chromatography).

Example 6

Preparation of 2R-Propyloctanoic Acid

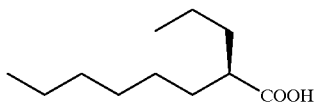

To a 40% aqueous solution of tetrabutylammonium hydroxide (1.4 ml) was added dimethoxyethane (2 ml) and toluene (2 ml), and concentrated. After this procedure was repeated (×4), anhydrous tetrabutylammonium hydroxide was prepared. To a solution of the compound prepared in example 5 (400 mg) in tetrahydrofuran (2 ml) was added dropwise 30% aqueous solution hydrogen peroxide (0.21 ml) and a solution of anhydrous tetrabutylammonium hydroxide (the prepared in above) in tetrahydrofuran (2 ml) at −20° C. The reaction mixture was stirred for 50 minute at −20° C. The mixture was quenched by 1.5N aqueous solution of sodium sulfite (1.4 ml), and stirred for 30 minute at room temperature. The mixture was concentrated, water and 2N aqueous solution of hydrochloric acid was added thereto, and the mixture was extracted with a mixture solution of ethyl acetate:isopropyl ether=1:4 (×2). The extract was washed with water (×2) and a saturated aqueous solution of sodium chloride, successively, dried over anhydrous sodium sulfate, and concentrated. To the residue was added isopropyl ether, insoluble matters were filtered, and the filtrate was concentrated. The residue was purified by silica gel column chromatography (hexane:ethyl acetate=19:1) to give the title compound (115 mg, 59.3% yield) having the following physical data.

TLC: Rf 0.46 (hexane:ethyl acetate=7:3); NMR (CDCl$_3$): δ 2.38 (1H, m,), 1.55 (2H, m), 1.53–1.20 (12H, m), 0.94 (3H, t, J=6.8 Hz), 0.90 (3H, t, J=6.8 Hz); IR (neat): ν 2959, 2932, 1707, 1470, 1420, 1379, 1289, 1215, 943 Optical purity: 99% e.e. (liquid chromatography).

Example 7

Preparation of N-(2S-(2-Propynyl)octanoyl)-(1S)-(−)-2,10-camphorsultam

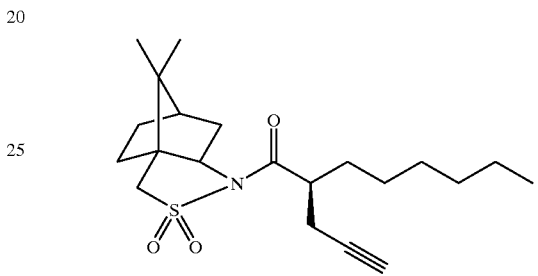

To a solution of diisopropylamine (6.7 ml) in tetrahydrofuran (13 ml) was added dropwise 1.6 M n-butyllithium in hexane solution (32 ml) at 0° C. The mixture was stirred for 20 minute at the same temperature. This solution was slowly added dropwise to the solution of the compound prepared in reference example 1 (16.0 g) in tetrahydrofuran (27 ml) at −78° C. After the mixture was stirred for 30 minute at the same temperature, and to this solution was added dropwise the mixture solution of propargyl bromide (5.2 ml), a solution of lithiumiodide (1.24 g) in tetrahydrofuran (5 ml) and dimethylindazolidione (7.6 ml). The reaction mixture was stirred for 1.5 hours at −78° C. and 2 hours at −30°C. The mixture was quenched by water, and concentrated. The residue was extracted with a mixture solution of hexane:ethyl acetate=1:1. The extract was washed with a saturated aqueous solution of sodium ammonium (×2), water (×3) and a saturated aqueous solution of sodium chloride, successively, dried over anhydrous sodium sulfate, and concentrated. The residue was purified by silica gel column chromatography (hexane:ethyl acetate=19:1→9:1) to give the title compound (14.6 g, 83.0% yield (2 steps from (1S)-(−)-2,10-camphorsultam) having the following physical data.

TLC: Rf 0.55 (toluene:ethyl acetate=19:1); NMR (CDCl$_3$): δ 3.93 (1H, dd, J=7.1, 5.4 Hz), 3.53 (1H, d, J=13.9 Hz), 3.45 (1H, d, J=13.9 Hz), 3.21 (1H, m), 2.55 (2H, m), 2.11 (2H, m), 1.99 (1H, t, J=2.6 Hz), 1.87 (4H, m), 1.57–1.23 (11H, m), 1.19 (3H, s), 0.98 (3H, s), 0.87 (3H, t, J=6.7 Hz); IR (KBr): ν 3318, 2970, 2945, 2850, 1690, 1470, 1458, 1433, 1418, 1397, 1323, 1280, 1270, 1238, 1220, 1165, 1134, 1110, 1061, 1040, 947 cm$^{-1}$; diastereoisomer excess: 96.8% (liquid chromatography).

Thus obtained title compound was recrystallized from a mixture solution of isopropyl alcohol:water=5:1 to give the title compound having the following physical data.

diastereoisomer excess: 99.4% (liquid chromatography).

Example 8(a)

Preparation of 2S-(2-Propynyl)octanoic Acid

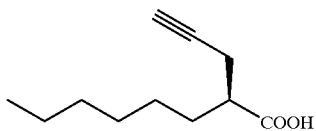

To a solution of the compound prepared in example 7 [400 mg, diastereoisomer excess: 96.8% (liquid chromatography)] in dimethoxyethane (4 ml) was added 2-methyl-2-butene (0.33 ml) and 30% aqueous solution hydrogen peroxide (0.22 ml). To vigorously stirring this mixture was added dropwise 40% aqueous solution tetrabutylammonium hydroxide (1.4 ml). The reaction mixture was stirred for 10 minute at −10° C. The mixture was quenched by 1.5N aqueous solution of sodium sulfite (1.5 ml), and stirred for 30 minute at room temperature. The mixture was concentrated, water was added thereto, and the mixture was extracted with a mixture solution of ethyl acetate:isopropyl ether=1:4 (×2). To the water layer was added 2N aqueous solution of hydrochloric acid, and the mixture was extracted with isopropyl ether (×2). The extract was washed with water (×2) and a saturated aqueous solution of sodium chloride, successively, dried over anhydrous sodium sulfate, and concentrated. The residue was purified by silica gel column chromatography (hexane:ethyl acetate=9:1) to give the title compound (172 mg, 89.6% yield) having the following physical data.

TLC: Rf 0.55 (toluene:ethyl acetate=19:1); NMR (CDCl$_3$): δ 2.62 (1H, m), 2.54 (1H, ddd, J=16.6, 6.8, 2.6 Hz), 2.43 (1H, ddd, J=16.6, 6.8, 2.6 Hz), 2.03 (1H, t J=2.6 Hz), 1.70 (2H, m), 1.30 (8H, m), 0.90 (3H, t, J=6.8 Hz); IR (neat): ν 3312, 2930, 1717, 1559, 1541, 1509, 1458, 1289, 938 cm$^{-1}$; Optical purity: 96.4% e.e. (gas chromatography).

Example 8(b)

Preparation of 2S-(2-Propynyl)octanoic Acid

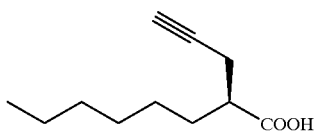

To a mixture solution of the compound prepared in example 7 [400 mg, diastereoisomer excess 96.8% (liquid chromatography)] in tetrahydrofuran (16 ml) and water (2.6 ml) was added dropwise 30% aqueous solution hydrogen peroxide (0.22 ml) at 0° C. To this solution was added dropwise 2N aqueous solution of lithium hydroxide (2.1 ml). The reaction mixture was stirred for 2 hours at −10° C. and 1.5 hours at room temperature.

The mixture was quenched by 1.5N aqueous solution of sodium sulfite (5.6 ml), and stirred for 3 hours at room temperature. The mixture was concentrated, water was added thereto, and the mixture was extracted with a mixture solution of ethyl acetate:isopropyl ether=1:4 (×2). The extract was washed with water (×3) and a saturated aqueous solution of sodium chloride. To all water layer was added 2N aqueous solution of hydrochloric acid, and the mixture was extracted with isopropyl ether (×2). The extract was washed with water (×2) and a saturated aqueous solution of sodium chloride, successively, dried over anhydrous sodium sulfate, and concentrated. The residue was purified by silica gel column chromatography (hexane:ethyl acetate=9:1) to give the title compound (169 mg, 88% yield) having the following physical data.

TLC: Rf 0.55 (toluene:ethyl acetate=19:1), NMR (CDCl$_3$): δ 2.62 (1H, m), 2.54 (1H, ddd, J=16.6, 6.8, 2.6 Hz), 2.43 (1H, ddd, J=16.6, 6.8, 2.6 Hz), 2.03 (1H, t J=2.6 Hz), 1.70 (2H, m), 1.30 (8H, m), 0.90 (3H, t, J=6.8 Hz); IR (neat): ν 3312, 2930, 1717, 1559, 1541, 1509, 1458, 1289, 938 cm$^{-1}$; cm$^{-1}$; Optical purity: 96.8% e.e. (gas chromatography).

Example 9(a)

Preparation of 2R-Propyloctanoic Acid

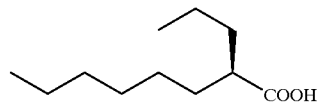

To a solution of the compound prepared in example 8(a) (114 mg) in ethyl acetate (2 ml) was added palladium carbon (10 mg). The reaction mixture was stirred for 10 minute at room temperature under an atmosphere of hydrogen gas. The reaction mixture was filtrated through Celite (being on sale), and concentrated. The residue was purified by silica gel column chromatography (hexane:ethyl acetate= 9:1→4:1) to give the title compound (113 mg, 97% yield) having the following physical data.

TLC: Rf 0.34 (hexane:ethyl acetate=4:1); NMR (CDCl$_3$): δ 2.46–2.27 (1H, m), 1.75–1.12 (14H, m), 0.96–0.75 (6H, IR (neat): ν 2959, 2932, 2860, 1708, 1466, 1419, 1380, 1290, 1255, 1217, 1112, 944 cm$^{-1}$.

Example 9(b)

Preparation of 2R-Propyloctanoic Acid

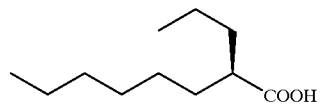

To a solution of the compound prepared in example 8(a) [3.0 g, 99.3% e.e. (liquid chromatography)] in diethoxyethane (75 ml) was added 5% palladium carbon (600 mg, 50% containing in water). The reaction mixture was stirred for 1 hour under an atmosphere of hydrogen gas and 5 atmospheric pressure, further stirred for 4 hours at 30° C. The reaction mixture was cooled down at room temperature, filtrated through Celite (being on sale), and the filtrate was concentrated. The residue was dissolved in the mixture solution of hexane:ethyl acetate=5:1, and extracted with 2N aqueous solution of sodium hydroxide. To the water layer was added conc. hydrochloric acid, and the mixture was extracted with the mixture solution of hexane:ethyl acetate= 5:1. The extract was washed with water and a saturated aqueous solution of sodium chloride, successively, dried over anhydrous magnesium sulfate, and concentrated to give the title compound (2.7 g, 89% yield) having the following physical data.

TLC: Rf 0.34 (hexane:ethyl acetate=4:1);

Optical purity: 96.8% e.e. (liquid chromatography).

Industrial Application Field

According to the present invention, optically active 2R-propyloctanoic acid or its preparation intermediate compounds can be obtained as medicaments at an optical purity equal to or higher than that of the conventional processes and at few reaction steps efficiently.

Specifically, 2R-propyloctanoic acid is obtained at 90.0% e.e. (the process of JP-A-8-291106) or 96.0% e.e. (the process of JP-A-8-295648) in the conventionally know processes, whereas it is obtained at a high optical purity of 95–99% e.e. in the process of the present invention.

Furthermore, in the preparation of optically active 2R-propyloctanoic acid, the process of the present invention is by far more excellent than the conventional processes in terms of the chemical yield and the number of the reaction steps. Specifically, the total synthetic yield is 5.9% at 6 stages from dimethyl hexylmalonate (the process of JP-A-8-291106) and the total synthetic yield is 20.1% at 5 stages from pentanoyl chloride (the process of JP-A-8-295648) in the conventional processes, whereas 2R-propyloctanoic acid can be obtained at a high chemical yield of a total synthetic yield of 42.5–72.1% and by few step numbers of 4 stages from octanoyl chloride.

As discussed above, the process of the present invention would be a process suitable for synthesizing 2R-propyloctanoic acid industrially at a large scale.

What is claimed is:

1. A process for the preparation of optically active 2S-(2-propenyl)octanoic acid, which comprises hydrolyzing N-(2S-(2-propenyl) octanoyl)-(1S)-(−)-2,10-camphorsultam.

2. The process of claim 1 further comprising the preparation of optically active 2R-propyloctanic acid, said process comprising the step of reducing the optically active 2S-(2-propenyl)octanoic acid obtained in claim 1.

3. A process for the preparation of optically active 2S-(2-propynyl)octanoic acid, which comprises hydrolyzing optically active N-(2S-(2-propynyl)octanoyl)-(1S)-(−)-2,10-camphorsultam.

4. The process of claim 3 further comprising the preparation of optically active 2R-propylooctonic acid, said process comprising the step of reducing the optically active 2S-(2-propynl)octanoic acid obtained in claim 3.

5. A process for the preparation of optically active 2-R-propyloctanoic acid, which comprises hydrolyzing optically active N-(2R-(2-propyl)octanoyl)-(1S)-(−)-2,10-camphorsultam.

* * * * *